(12) United States Patent
Kumar et al.

(10) Patent No.: US 9,962,236 B1
(45) Date of Patent: May 8, 2018

(54) SPLATTER REDUCTION IN A SMALL HEAD CONTRA-ANGLE PROPHY

(71) Applicants: Ajay Kumar, Palmdale, CA (US);
Hamid Reza Abedi, Irvine, CA (US);
Vishu Shah, Diamond Bar, CA (US)

(72) Inventors: Ajay Kumar, Palmdale, CA (US);
Hamid Reza Abedi, Irvine, CA (US);
Vishu Shah, Diamond Bar, CA (US)

( * ) Notice: Subject to any disclaimer, the term of this patent is extended or adjusted under 35 U.S.C. 154(b) by 0 days. days.

(21) Appl. No.: 15/253,442

(22) Filed: Aug. 31, 2016

Related U.S. Application Data

(63) Continuation of application No. 15/236,685, filed on Aug. 15, 2016.

(51) Int. Cl.
| | | |
|---|---|---|
| *A61C 1/16* | (2006.01) | |
| *A61C 1/12* | (2006.01) | |
| *A61C 17/00* | (2006.01) | |
| *A61C 17/24* | (2006.01) | |

(52) U.S. Cl.
CPC .................. *A61C 1/16* (2013.01); *A61C 1/12* (2013.01); *A61C 17/005* (2013.01); *A61C 17/24* (2013.01)

(58) Field of Classification Search
CPC ..................................... A61C 1/16; A61C 3/06
See application file for complete search history.

(56) References Cited

U.S. PATENT DOCUMENTS

| | | | |
|---|---|---|---|
| 1,694,636 A | 12/1928 | Barker | |
| 2,039,278 A | 5/1936 | Blanchard | |
| 2,738,528 A | 3/1956 | Fridge, Sr. | |
| 2,943,343 A | 7/1960 | Jankelson | |
| 3,195,537 A | 7/1965 | Blasi | |
| 3,542,372 A * | 11/1970 | Edwardson | B23Q 11/005 277/309 |
| 3,621,577 A | 11/1971 | Spinello | |
| 3,727,315 A | 4/1973 | Spinello | |
| 3,786,566 A * | 1/1974 | Jelicic | A61C 1/16 221/179 |
| 3,939,599 A | 2/1976 | Henry et al. | |
| 4,259,071 A | 3/1981 | Warden et al. | |
| 4,274,173 A | 6/1981 | Cohen | |
| 4,424,036 A * | 1/1984 | Lokken | A61C 17/005 433/116 |
| 5,028,233 A | 7/1991 | Witherby | |
| 5,131,846 A * | 7/1992 | Hall | A61C 1/16 433/116 |

(Continued)

*Primary Examiner* — Ralph Lewis
(74) *Attorney, Agent, or Firm* — Innovation Capital Law Group, LLP; Vic Lin

(57) ABSTRACT

A splatter guard for a dental cleaning tool eliminates the splatter by gathering splatter first on the outer lower one-third to one-half of the fructoconical prophy cup using combination of vanes and the dimples. As the splatter migrates upwards, the splatter guard wipes off the splatter. The reason the splatter guard is constructed smaller than the cup is because it allows the cup to flex outward without interfering during use thereof. The splatter guard can be attached several different ways, including slide in, snap on, secured between two half-housing members, or formed integrally with the housing, for example. The drive train is housed in a partial split contra angle housing which allows accurate positioning of the gears as it is required to ensure that the cup rotates concentrically and remains in touch with the knife edge of the splatter guard.

20 Claims, 8 Drawing Sheets

(56) References Cited

U.S. PATENT DOCUMENTS

| | | | |
|---|---|---|---|
| 5,348,473 | A | 9/1994 | Kivlighan |
| 5,380,202 | A | 1/1995 | Brahler |
| 5,484,284 | A | 1/1996 | Bailey |
| 5,531,599 | A | 7/1996 | Bailey |
| 5,584,690 | A | 12/1996 | Maassarani |
| 5,642,995 | A | 7/1997 | Bailey |
| 5,775,905 | A | 7/1998 | Weissenfluh et al. |
| 6,146,140 | A | 11/2000 | Bailey |
| 7,422,433 | B2 | 9/2008 | Carron et al. |
| 7,762,813 | B2 | 7/2010 | Seals et al. |
| 8,566,993 | B1 | 10/2013 | Ukaj |
| 8,597,022 | B2 | 12/2013 | Carron et al. |
| 8,784,102 | B1 * | 7/2014 | Kumar ............... A61C 1/141 433/116 |
| 9,017,073 | B2 | 4/2015 | Madry et al. |
| 2006/0292522 | A1 | 12/2006 | Lees et al. |
| 2009/0035719 | A1 | 2/2009 | Seals et al. |
| 2010/0035205 | A1 | 2/2010 | Wang et al. |
| 2014/0141386 | A1 | 5/2014 | Madry et al. |

\* cited by examiner

SPLATTER REDUCTION IN A SMALL HEAD CONTRA-ANGLE PROPHY

CROSS-REFERENCE TO RELATED APPLICATION

This application is a continuation application of U.S. Non-Provisional Application having Ser. No. 15/236,685 filed Aug. 15, 2016 and claims benefit under 35 U.S.C. § 119(e), which is hereby incorporated by reference herein in its entirety.

BACKGROUND OF THE INVENTION

1. Field of the Invention

One or more embodiments of the invention relates generally to splatter reduction in a small head contra-angle prophy. More particularly, the invention relates to splatter reduction in a small head contra-angle prophy by usage of a splatter guard and micro-features on the outside of the cup.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Most prophy pastes contain pumice, usually about 30 microns in diameter. These pastes provide no true polishing effect and leave the tooth surface with only a matte satin-like finish. Because of the large particle size of the traditional pumice and silica particles used, the pumice particles create an overwhelming gritty mouth feel, and inevitably, cause spattering during use as a result of composition non-homogeneity and centrifugal forces on the pumice particles. As a result, such compositions are perceived as messy, unpleasant and unsatisfactory by patients and hygienists alike.

Splatter is a long-standing problem that occurs during the tooth cleaning procedure. This happens when the cleaning paste and saliva are thrown from the edges of the prophy cup due to the centrifugal force generated by the spinning action of the cup, which is approximately 6 millimeters in diameters and may rotate at speeds of up to 5,000 RPM.

Specifically, the abrasive slurry between the cup and tooth surfaces attaches with the patient's saliva and migrates to the outer edges of the cup. As the cup spins, this bale like structure composed of abrasive slurry and saliva is thrown from the cup as a contaminated splatter. Operating the prophy cup into the spaces under the gums often adds blood pathogens to the slurry, raising the level of contamination in the splatter. As a result, there is a danger of the attending practitioner being infected from the contaminated splatter during the tooth cleaning procedure.

To help prevent splatter, various devices have been proposed. One such device is disclosed by Jankelson (U.S. Pat. No. 2,943,343). In Jankelson '343, the splatter guard goes inside and around the periphery of the cup to prevent it from flexing during polishing procedure, which is required for it to function.

Accordingly, there remains a definite need for protection from bodily fluids in dentistry and, more particularly, an effective device to contain splatter of cleaning paste and patient bodily fluids during the tooth cleaning procedure so that the attending practitioner is protected from contamination.

SUMMARY OF THE INVENTION

Embodiments of the present invention provide a hand piece comprising a rotating member; and a splatter guard attached to a housing of the hand piece, the splatter guard having a proximate edge, proximate the rotating member, and a distal edge, distal the rotating member, the proximate edge abutting the rotating member, wherein the distal edge has a first thickness and the proximate edge has a second, smaller thickness.

In some embodiments, the rotating member is a cleaning cup of a dental tool. In some embodiments, the splatter guard has a mounting end and a distal, opposite end, wherein the distal, opposite end, at the proximate edge does not reach a longitudinal end of the cleaning cup.

In some embodiments, the splatter guard narrows to a single razor edge at the proximate edge. In other embodiments, the splatter guard narrows to multiple razor edges at the proximate edge.

In some embodiments, the splatter guard is formed from a single material. In other embodiments, the splatter guard is formed from a first material, at the distal edge and a second material at the proximate edge, wherein the first material is more rigid than the second material.

In some embodiments, the splatter guard attaches to the housing via a snap on configuration. In other embodiments, the splatter guard attaches to the housing view a slide-in configuration. In further embodiments, the splatter guard is molded into and integral with the housing. In additional embodiments, the splatter guard includes at least two tabs that interconnect to housing halves of the housing. Often in this embodiment, one of the housing halves has a completely circular molded back end.

Embodiments of the present invention further provide a splatter guard, comprising a mounting end for attachment to a hand piece; a distal end opposite the mounting end; a distal edge spanning between the connection end and the distal end, the distal edge being distal to a cleaning cup when the splatter guard is attached to the hand piece; and a proximate edge spanning between the connection end and the distal end, the proximate edge being proximate to the cleaning cup when the splatter guard is attached to the hand piece, wherein the proximate edge has a first thickness and the distal edge has a second, greater thickness.

Embodiments of the present invention also provide a dental cleaning tool comprising a cleaning cup; and a splatter guard attached to a housing of the hand piece, the splatter guard having a proximate edge, proximate the cleaning cup, and a distal edge, distal the cleaning cup, the proximate edge abutting the cleaning cup, the splatter guard including a mounting end for attachment to the dental cleaning tool and a distal end opposite the mounting end, wherein the distal edge has a first thickness and the proximate edge has a second, smaller thickness; and the distal end of the proximate edge does not reach a longitudinal end of the cleaning cup.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

FIG. 9A further illustrates a solid, completely circular back end of the hand piece;

Figure 1:
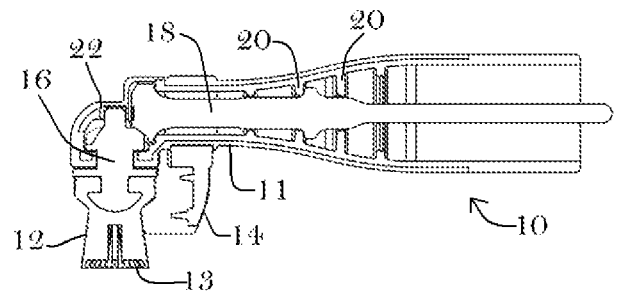
FIG. 1 illustrates a cross-sectional view of a Doriot-type hand piece having a splatter guard according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Devices that are in at least general communication with each other need not be in continuous communication with each other, unless expressly specified otherwise. In addition, devices that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

Broadly, embodiments of the present invention provide a splatter guard for a dental cleaning tool that eliminates the splatter by gathering splatter first on the outer lower one-third to one-half of the fructoconical prophy cup using combination of vanes and the dimples. As the splatter migrates upwards, the splatter guard wipes off the splatter. The reason the splatter guard is constructed smaller than the cup is because it allows the cup to flex outward without interfering during use thereof. The splatter guard can be attached several different ways, including slide in, snap on, secured between two half-housing members, or formed integrally with the housing, for example. The drive train is housed in a partial split contra angle housing which allows accurate positioning of the gears as it is required to ensure that the cup rotates concentrically and remains in touch with the knife edge of the splatter guard.

Figure 2:
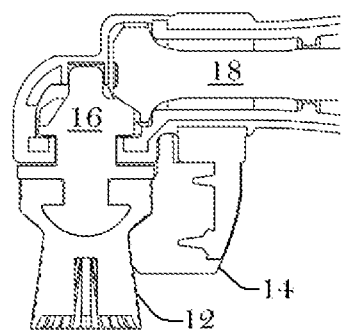
FIG. 2 illustrates a detailed cross-sectional view of the cleaning cup mounted on the hand piece of FIG. 1.

Referring to FIGS. 1 and 2, a Doriot-type hand piece 10, also referred to as hand piece 10, includes a cleaning cup 12, also referred to an prophy cup 12, disposed at an angle to the longitudinal axis of the hand piece 10. A splatter guard 14 may be mounted to an underside 11 of the hand piece 10 so that one edge of the splatter guard 14 fits closely alongside a portion of the cleaning cup 12. The splatter guard 14 is disposed a distance away from an end 13 of the cleaning cup 12. This distance is preferably from about 2 to about 5 mm, usually about 3 mm.

The hand piece 12 can include a short shaft 16 that connects to the cleaning cup 12. The short shaft 16 is driven by a long shaft 18. One or more mounting brackets 20 may ensure secure fixation of the long shaft 18. One or more mounting brackets 22 may ensure secure fixation of the short shaft 16.

Figure 3:
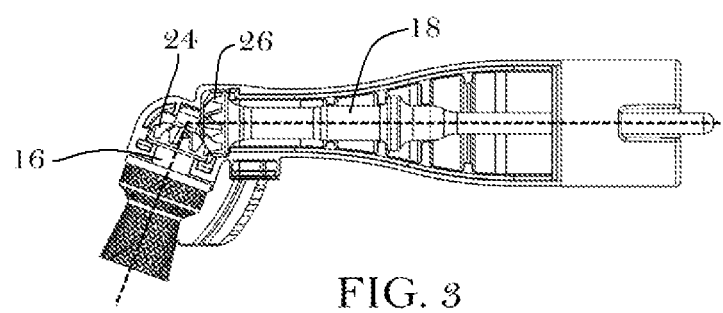
FIG. 3 illustrates a partially cut-away view of a contra angle Doriot-type hand piece according to an exemplary embodiment of the present invention.

In a contra angle design, as shown in FIG. 3, the angles often make an unwanted noise caused by contact between the drive gear 26 and the shaft 18 of the driven gear 24. This leads to an unpleasant dental experience for the patient who may already be feeling anxious. Additionally, the unwanted contact causes a rough operation of the gears as opposed to a desired smooth operation. It also causes unnecessary wear and tear on the angle gears, and dentists may need to disposed of the angle sooner than should be necessary. The main culprit for this noise is that there is nothing to secure the drive gear within the body. The drive gear is essentially floating within the body.

Axial support of both shafts 16, 18 is desired because, during meshing of the gears, a downward force tries to move the gears apart. In the preferred embodiment, both gears 24, 26 are completely secured using retentive features, such as mounting brackets 20, 22, in the housing to prevent any axial separation of the two gears 24, 26.

A contra angle design hand piece 30 may be made splatter free through the use of the splatter guard 14. In this configuration, both gears 24, 26 are completely secured using retentive features in the housing to prevent any axial separation of the two gears 24, 26. Further, having the gears mesh at an angle and having the shaft 18 completely straight eliminates the drawback of having a bent shaft and over flexion of the shaft.

Figure 4A:
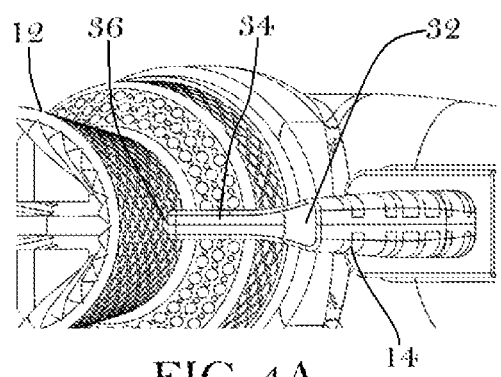
FIG. 4A illustrates a detailed bottom view showing the splatter guard against a cleaning cup.
Figure 4B:
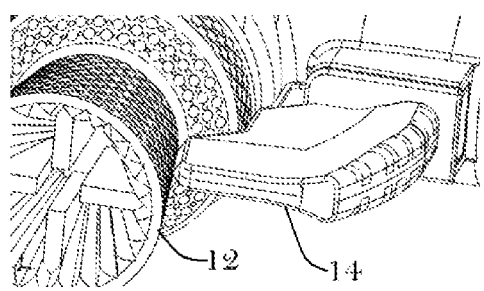
FIG. 4B illustrates a detailed perspective view showing the splatter guard against the cleaning cup.

Referring now to FIGS. 4A and 4B, the splatter guard 14 may be disposed adjacent the cleaning cup 12, as described above. The splatter guard 14 may be designed so that it is thicker at a distal end 32 (relative to the cleaning cup 12) to provide structural rigidity, and thinner along a proximal end 34 to reduce the co-efficient of friction against the cleaning cup 12. A cleaning edge 36 of the splatter guard 14 may be made with a single point, as shown in FIG. 4B, for example.

In some embodiments the distal end 32 of the splatter guard 14 may be made out of a different material, such as from a different engineering resin, so the distal end 32 that requires rigidity is made out of engineering resin such as polycarbonate, and the portion of the splatter guard 14 that touches the cleaning cup 12 is made out of an engineering resin that is soft and pliable, such as Versaflex and/or rubber.

In other embodiments, the entire splatter guard 14 may be made out of a single material, where the varied thickness between the distal end 32 and the proximate end 34 can provide a similar effect as the different material.

As discussed above, the splatter guard 14 is made shorter than the cleaning cup 12, so that the cleaning cup 12 can flex outward on the tooth surface during the cleaning process.

Figure 5A:
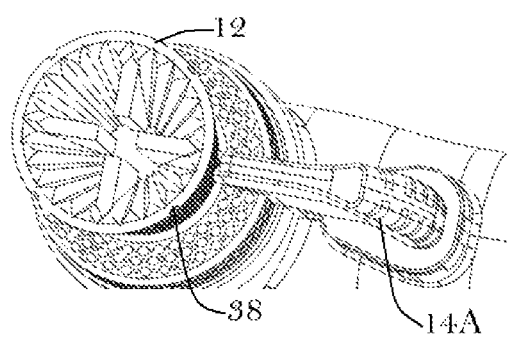
FIG. 5A illustrates a detailed bottom perspective view of a splatter guard against a cleaning cup.
Figure 5B:
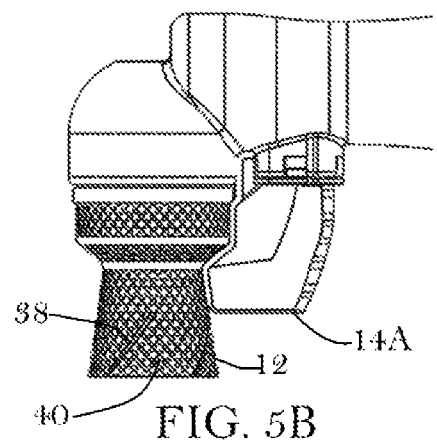
FIG. 5B illustrates a detailed side view of the splatter guard against the cleaning cup.
Figure 6:
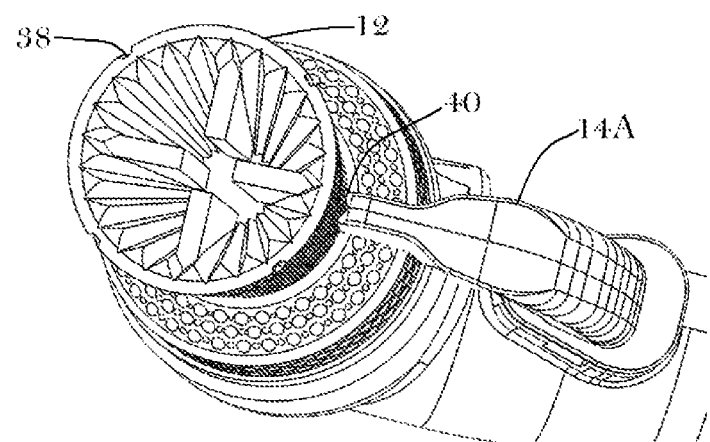
FIG. 6 illustrates a detailed bottom perspective view of a splatter guard having a dual cleaning edge according to an exemplary embodiment of the present invention.

Referring to FIGS. 5A and 5B, a splatter guard 14 may be designed with dual cleaning edges 40, as better shown in FIG. 6. Regardless of whether dual cleaning edges 40 or a single cleaning edge 36 are used, the edge 40, 36 may be extended to a razor thin edge at the cleaning cup 12 contacting edge to reduce frictional losses and prevent cup slippage.

In some embodiments, the cleaning cup 12 may include dimples 40 to collect the slurry. In some embodiments, the dimples 40 may be similar to those shown in U.S. Pat. No. 8,784,102, the contents of which are herein incorporated by reference. In some embodiments, the cleaning cup may further include conical vanes 38 that spiral, typically clockwise, upwards to direct the slurry toward the splatter guard 14. The conical vanes 38 typically are only disposed in the area where the splatter guard 14 ends—in other words, the conical vanes 38 are disposed from the end 13 of the cleaning cup 12 to the bottommost area where the splatter guard 14 contacts the cleaning cup 12. The conical vanes 38 can direct the movement of fluid upwards toward the splatter guard 14 and allows the cleaning cup 12 to flex outward as it is thinned out in these areas.

Figure 7:
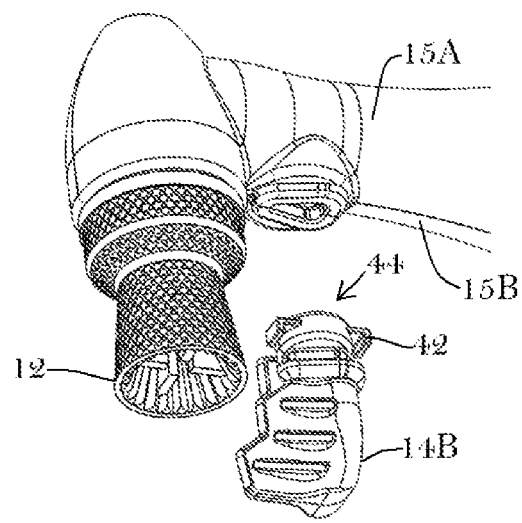
FIG. 7 illustrates an exploded side view of a splatter guard on a hand piece.
Figure 8A:
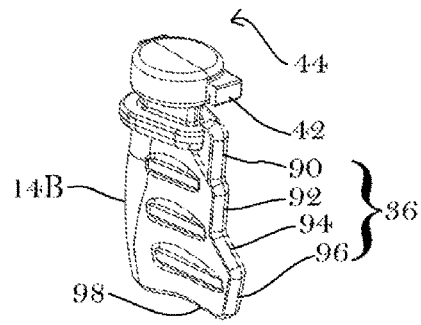
FIG. 8A illustrates a perspective view of a splatter guard according to an exemplary embodiment of the present invention.
Figure 9A:
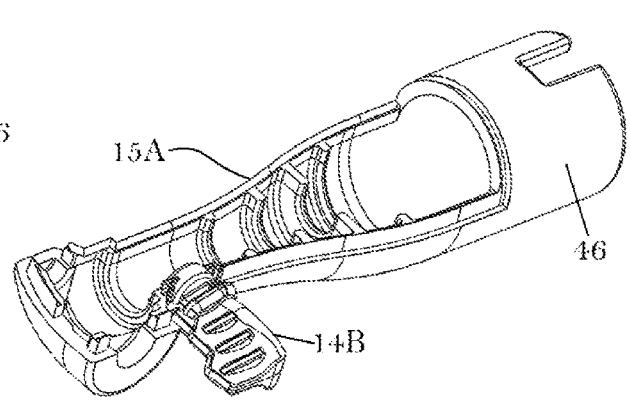
FIG. 9A illustrates a perspective view of a splatter guard fitted into half of the Doriot-type hand piece.
Figure 8B:
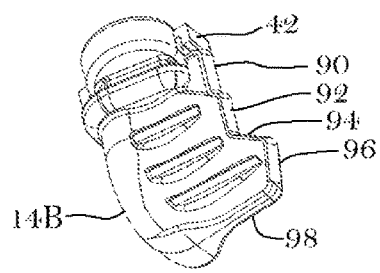
FIG. 8B illustrates a bottom perspective view of the splatter guard of FIG. 8A.
Figure 9B:
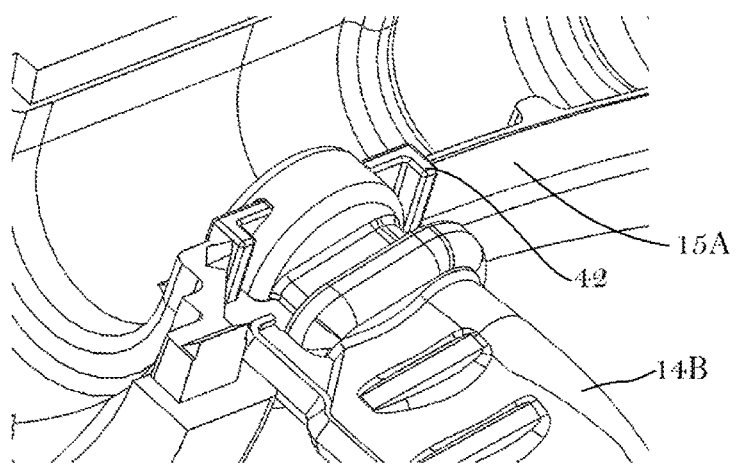
FIG. 9B illustrates a detailed perspective view of the splatter guard fitted into the hand piece of FIG. 9A.

Referring now to FIGS. 7, 8A and 8B, a splatter guard 14B can include tabs 42 on a mounting region 44 of the splatter guard 14B. In this embodiment, the splatter guard 14B may be disposed between two housing halves 15A, 15B. Typically, two tabs 42 may be disposed on the mounting region 44 of the splatter guard 14B, as shown, however, other quantities of tabs 42 may be used within the scope of the present invention. When two tabs 42 are provided on the splatter guard 14B, typically these two tabs 42 are disposed so that a portion of each of the tabs 42 are retained in both of the housing halves 15A, 15B. FIGS. 9A and 9B show the splatter guard 14B disposed in a housing half 15A. A backend 46 of the housing half 15A is molded completely circular, rather than being cut in half like the remainder of the housing. This ensures that the Doriot connection with the hand piece can provide enough friction without creating large hoop stresses which can cause the housing to split during insertion.

In some embodiments, rather than being a separate piece, the splatter guard 14B may be molded integrally with one of the housing halves 15A, 15B. This design would ensure that the splatter guard 14B is properly positioned and aligned, and not moved or removed from the hand piece 10.

The splatter guards according to various embodiments of the present invention may be attached to the hand piece 10 by various means. As discussed above, the splatter guard 14B may be disposed between two halves 15A, 15B of the hand piece 10.

Figure 10B:
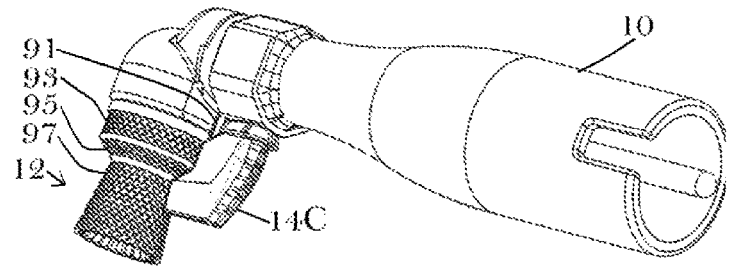
FIG. 10B illustrates an exploded side view of the cleaning cup with the snap on splatter guard removed, showing spiral grooves formed along an exterior surface thereof.
Figure 10A:
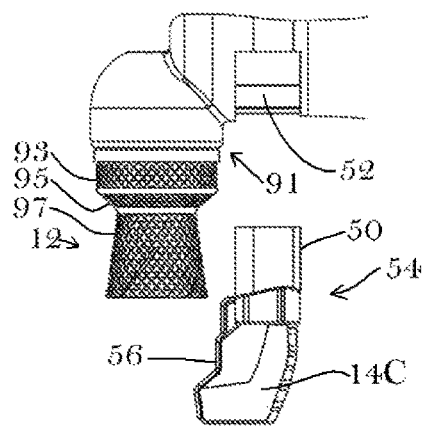
FIG. 10A illustrates a perspective view of a Doriot-type hand piece having a snap on splatter guard installed according to an exemplary embodiment of the present invention.
Figure 10C:
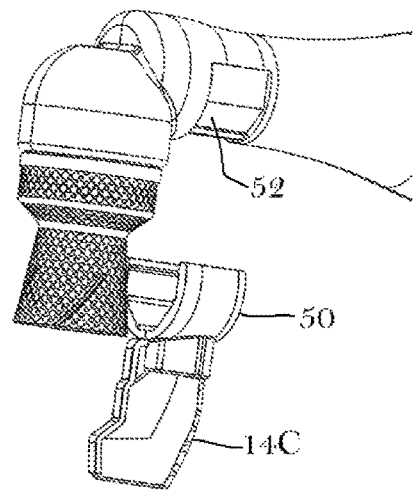
FIG. 10C illustrates a perspective view of a snap on the splatter guard according to an exemplary embodiment of the present invention.

In other embodiments, as shown in FIGS. 10A through 10C, a splatter guard 14C may be disposed with a snap on connector 50 formed onto a connection end 54 thereof. The snap on connector 50 may snap into a connection socket 52 formed in the hand piece 10. Like the embodiments described above, the splatter guard 14C may be formed from one or more components and may have a thicker distal end and a thinner, proximate end. Further, like the embodiments described above, the splatter guard 14C may include a wiping edge 56 that may include one or more edges for abutting against the cleaning cup 12.

Referring to FIGS. 8A, 8B, 10A and 10B shows various regions formed by the splatter guard 14B. These regions may include a first step 90, located adjacent the mounting region 44 of the splatter guard 14B and extending downward to form a first section of the cleaning edge 36. The first step 90 may abut an upper, first region 91 of the cleaning cup 12 and/or the hand piece 10. The second step 92 may extend from the first step 90 and is configured to abut a second region 93 of the cleaning cup 12. The third step 94 may extend from the second step 92 and is configured to abut a third region 95 of the cleaning cup 12. The fourth step 96 may extend from the third step 94 and is configured to abut a fourth region 97 of the cleaning cup. As discussed above, the fourth step 96 may end at a distal end 98 of the splatter guard 14B, where the distal end 98 is positioned a predetermined distance from the end 13 of the cleaning cup 12.

While the figures show, for example, the third region 94 as an angled region and the first region 90, second region 92 and fourth region 96 as being generally parallel with each other, various configurations are contemplated within the scope of the present invention, provided that each of the regions 90, 92, 94, 96 abut against the cleaning cup 12 in such a manner so that there are no gaps between the cleaning edge 36 and the cleaning cup 12.

Figure 11A:
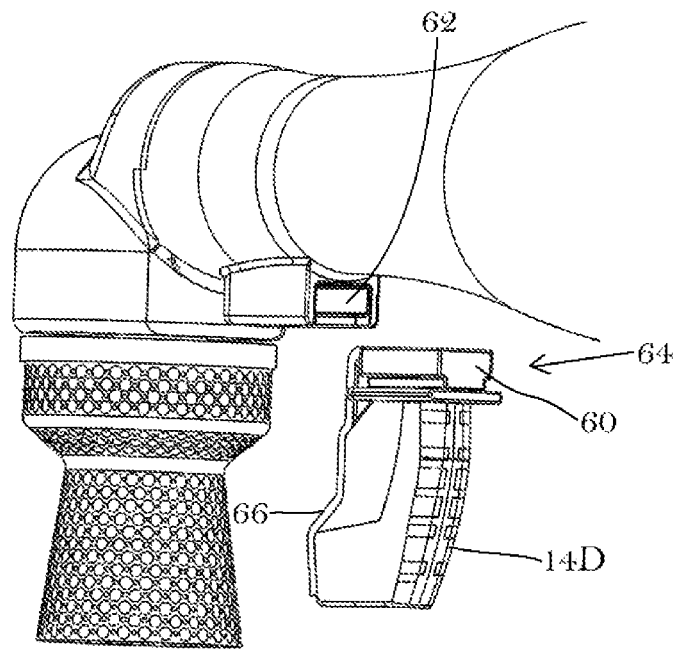
FIG. 11A illustrates a perspective view of a slide-in splatter guard according to an exemplary embodiment of the present invention.
Figure 11B:
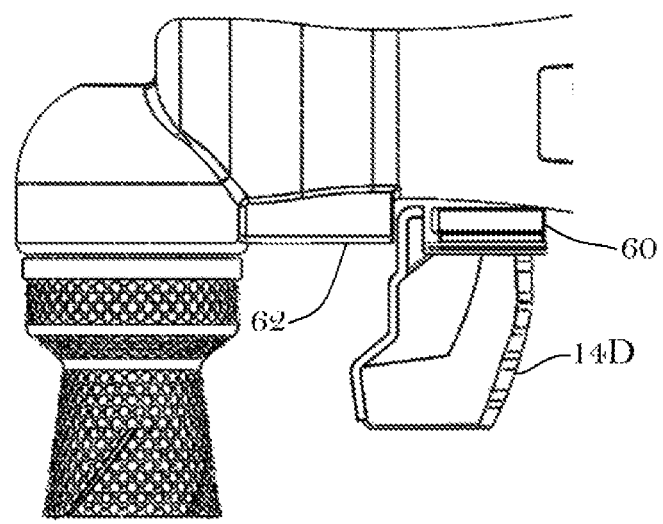
FIG. 11B illustrates a side view of the slide-in splatter guard of FIG. 11A, prior to sliding on the splatter guard mount.
Figure 11C:
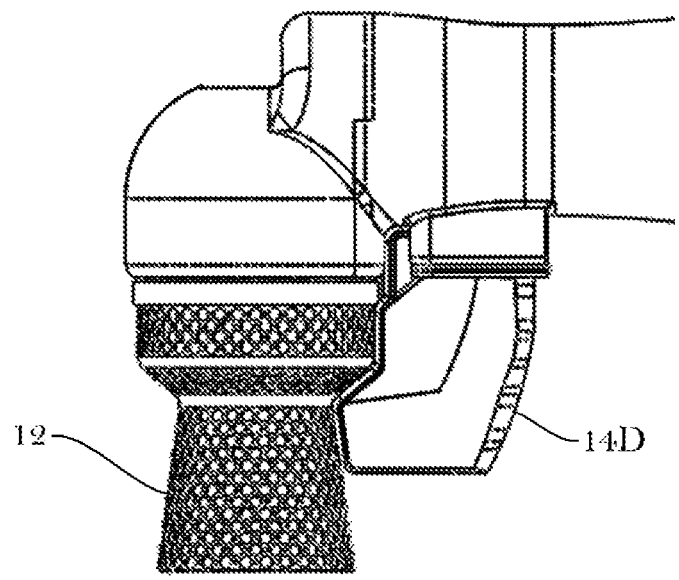
FIG. 11C illustrates a side view of the slide-in splatter guard of FIG. 11A, with the splatter guard slid fully in place against the cleaning cup.

Referring to FIGS. 11A through 11C, a slide-in configuration of a splatter guard 14D is shown. In this embodiment, a connector 60 may be disposed on a connection side 64 of the splatter guard 14D. The connector may slidably engage with a port 62 formed on the hand piece 10. Like the embodiments described above, the splatter guard 14D may be formed from one or more components and may have a thicker distal end and a thinner, proximate end. Further, like the embodiments described above, the splatter guard 14D may include a wiping edge 66 that may include one or more edges for abutting against the cleaning cup 12. In this embodiment, one or more locking features (not shown) may be used to help secure the splatter guard 14D at the proper position in the port 64. For example, a dimple may be formed on the connector 60 that mates with a protrusion within the port 62 to retain the splatter guard 14D at a proper position, with its wiping edge 66 abutting the cleaning cup 12.

Figure 12A:
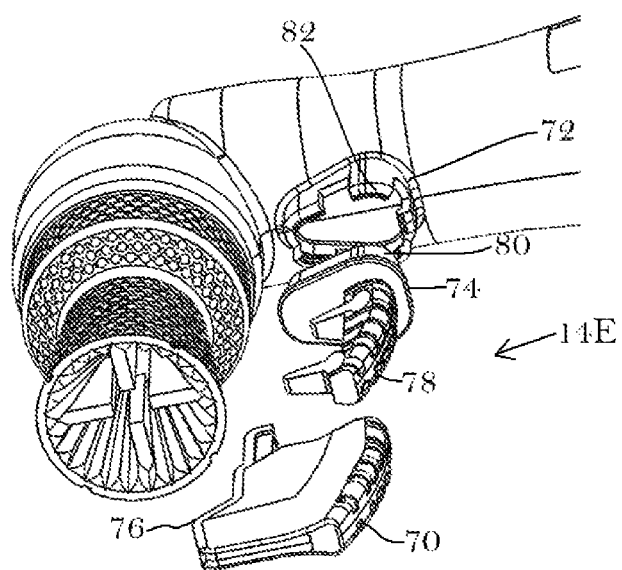
FIG. 12A illustrates a bottom perspective view of a snap on splatter guard according to an exemplary embodiment of the present invention.
Figure 12B:
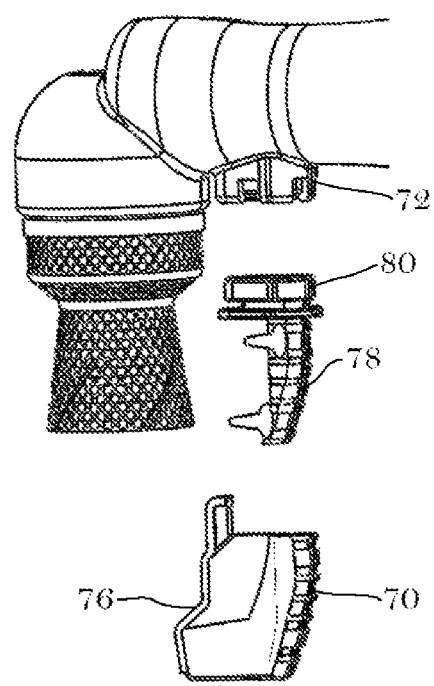
FIG. 12B illustrates an explodes side view of the snap on splatter guard of FIG. 12A.
Figure 6:
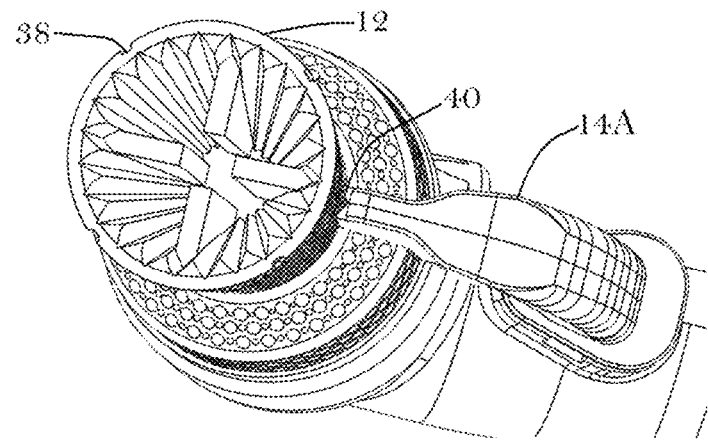

Referring to FIGS. 12A and 12B, a further alternate embodiment for attaching a splatter guard 14E to the hand piece 10 is shown. In this embodiment, the splatter guard 14E may include an outer shell 70 with a wiping edge 76 configured to be positioned adjacent the cleaning cup 12. An inner member 74 may have a protruding end 78 for fitting into and securing the outer shell 70. In some embodiments, the inner member 74 may be formed integrally with the outer shell 70. An attachment end 80 of the inner member 74 may be configured to fit into a port 72 formed on the hand piece 10. The port 72 may receive and secure the attachment end 80 by various manners, including, for example and as shown in FIG. 12A, a plurality of arms 82.

The various embodiments of the present invention, as described in greater detail above, provide a splatter guard that has a varying cross section, thick at the back, or distal, end, to make the splatter guard rigid, and thin in front (at the proximate end) to allow flexibility to prevent excessive friction. In some embodiments, the splatter guard can have multiple cleaning or wiping edges. In some embodiments, the splatter guard can be made out of a composite structure so the back, proximate end is made out of a rigid engineering resin and the front, proximate end is made out of a soft resin, such as Versaflex, to reduce friction.

As described above, the splatter guard can be attached to the hand piece in various manners, including snap on, slide-in, two shot molded with the housing, disposed between two housing halves, and the like.

The splatter guard does not extend beyond a longitudinal end (tooth contact end) of the cleaning cup. Typically, the splatter guard is shorter than the cup to allow the cup to flex during use.

The splatter guard can be put on a housing and be function with contra angle hand pieces, where, for example, the cleaning cup portion may be angled, with respect to the long shaft of the hand piece, from about 100 to about 130 degrees, typically about 110 degrees.

The housing can be designed with supports for the long gear/long shaft so that it does not axially translate, which keeps the gear engagement with the short gear consistent and ensures that the gears rotate concentrically. This is required to ensure that the cup rotates concentrically and never pulls away from the splatter guard.

Like the embodiments described above, the splatter guard 14E may be formed from one or more components and may have a thicker distal end and a thinner, proximate end. Further, like the embodiments described above, the wiping edge 76 of the splatter guard 14E may include one or more edges for abutting against the cleaning cup 12.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A hand piece comprising:
   a rotating member having a longitudinal axis; and
   a splatter guard attached to a housing of the hand piece, the splatter guard having a proximate edge, proximate the rotating member, and a distal edge, distal the rotating member, the proximate edge extending lengthwise along the longitudinal axis and abutting the rotating member, wherein
   the distal edge has a first thickness and the proximate edge has a second, smaller thickness; and
   the proximate edge, at an end distal to the housing, terminates prior to a longitudinal end of the rotating member.

2. The hand piece of claim 1, wherein the rotating member is a cleaning cup.

3. The hand piece of claim 1, wherein the splatter guard has a mounting end and a distal, opposite end, wherein the distal, opposite end, at the proximate edge does not extend beyond a longitudinal end of the rotating member.

4. The hand piece of claim 1, wherein the splatter guard narrows to a single razor edge at the proximate edge.

5. The hand piece of claim 1, wherein the splatter guard narrows to multiple razor edges at the proximate edge.

6. The hand piece of claim 1, wherein the splatter guard is formed from a first material, at the distal edge and a second material at the proximate edge, wherein the first material is more rigid than the second material.

7. The hand piece of claim 1, wherein the splatter guard attaches to the housing via a snap on configuration.

8. The hand piece of claim 1, wherein the splatter guard attaches to the housing via a slide-in configuration.

9. The hand piece of claim 1, wherein the splatter guard is molded into and integral with the housing.

10. The hand piece of claim 1, wherein the splatter guard includes at least two tabs that interconnect to the housing, securing the splatter guard to the housing.

11. The hand piece of claim 10, wherein the housing has a completely circular molded back end.

12. The hand piece of claim 1, further comprising one or more support members for supporting a long shaft gear within the housing, the long shaft gear configured to impart rotation to the rotating member.

13. A splatter guard, comprising:
    a mounting end for attachment to a hand piece;
    a distal end opposite the mounting end;
    a distal edge spanning between a connection end and the distal end, the distal edge being distal to a cleaning cup when the splatter guard is attached to the hand piece, the cleaning cup having a longitudinal axis; and
    a proximate edge spanning between the connection end and the distal end, the proximate edge extending lengthwise along the longitudinal axis and abutting the cleaning cup when the splatter guard is attached to the hand piece, wherein
    the proximate edge has a first thickness and the distal edge has a second, greater thickness; and
    the distal end of the proximate edge terminates prior to a longitudinal end of the cleaning cup.

14. The splatter guard of claim 13, wherein the splatter guard, at the distal end of the proximate edge, does not extend beyond a longitudinal end of the cleaning cup when the cleaning cup is attached to the hand piece.

15. The splatter guard of claim 13, wherein the splatter guard narrows to a single razor edge at the proximate edge.

16. The splatter guard of claim 13, wherein the splatter guard narrows to multiple razor edges at the proximate edge.

17. The splatter guard of claim 13, wherein the splatter guard is formed from a first material, at the distal edge and a second material at the proximate edge, wherein the first material is more rigid than the second material.

18. A dental cleaning tool comprising:
    a cleaning cup having a longitudinal axis; and
    a splatter guard attached to a housing of the hand piece, the splatter guard having a proximate edge, proximate the cleaning cup, and a distal edge, distal the cleaning cup, the proximate edge extending lengthwise along the longitudinal axis of the cleaning cup and abutting the cleaning cup, the splatter guard including a mounting end for attachment to the dental cleaning tool and a distal end opposite the mounting end, wherein
    the distal edge has a first thickness and the proximate edge has a second, smaller thickness; and
    the distal end of the proximate edge terminates prior to a longitudinal end of the cleaning cup.

19. The dental cleaning tool of claim 18, wherein the splatter guard narrows to one or more razor edges at the proximate edge.

20. The dental cleaning tool of claim 18, wherein the splatter guard is formed from a first material, at the distal edge and a second material at the proximate edge, wherein the first material is more rigid than the second material.

* * * * *

(12) EX PARTE REEXAMINATION CERTIFICATE (12705th)
United States Patent
Kumar et al.

(10) Number: US 9,962,236 C1
(45) Certificate Issued: Sep. 17, 2024

(54) SPLATTER REDUCTION IN A SMALL HEAD CONTRA-ANGLE PROPHY

(71) Applicants: Ajay Kumar, Palmdale, CA (US); Hamid Reza Abedi, Irvine, CA (US); Vishu Shah, Diamond Bar, CA (US)

(72) Inventors: Ajay Kumar, Palmdale, CA (US); Hamid Reza Abedi, Irvine, CA (US); Vishu Shah, Diamond Bar, CA (US)

(73) Assignee: AKHA, LLC, Irvine, CA (US)

Reexamination Request:
No. 90/019,421, Feb. 15, 2024

Reexamination Certificate for:
Patent No.: 9,962,236
Issued: May 8, 2018
Appl. No.: 15/253,442
Filed: Aug. 31, 2016

Related U.S. Application Data

(63) Continuation of application No. 15/236,685, filed on Aug. 15, 2016, now abandoned.

(51) Int. Cl.
*A61C 17/00* (2006.01)
*A61C 1/12* (2006.01)
*A61C 3/00* (2006.01)

(52) U.S. Cl.
CPC .............. *A61C 17/005* (2013.01); *A61C 1/12* (2013.01); *A61C 3/00* (2013.01)

(58) Field of Classification Search
CPC ........... A61C 17/005; A61C 1/12; A61C 3/06; A61C 1/16; A61C 17/24
USPC .................. 433/165, 166, 124, 125, 126, 116
See application file for complete search history.

(56) References Cited

To view the complete listing of prior art documents cited during the proceeding for Reexamination Control Number 90/019,421, please refer to the USPTO's Patent Electronic System.

*Primary Examiner* — Terrence R Till

(57) ABSTRACT

A splatter guard for a dental cleaning tool eliminates the splatter by gathering splatter first on the outer lower one-third to one-half of the fructoconical prophy cup using combination of vanes and the dimples. As the splatter migrates upwards, the splatter guard wipes off the splatter. The reason the splatter guard is constructed smaller than the cup is because it allows the cup to flex outward without interfering during use thereof. The splatter guard can be attached several different ways, including slide in, snap on, secured between two half-housing members, or formed integrally with the housing, for example. The drive train is housed in a partial split contra angle housing which allows accurate positioning of the gears as it is required to ensure that the cup rotates concentrically and remains in touch with the knife edge of the splatter guard.

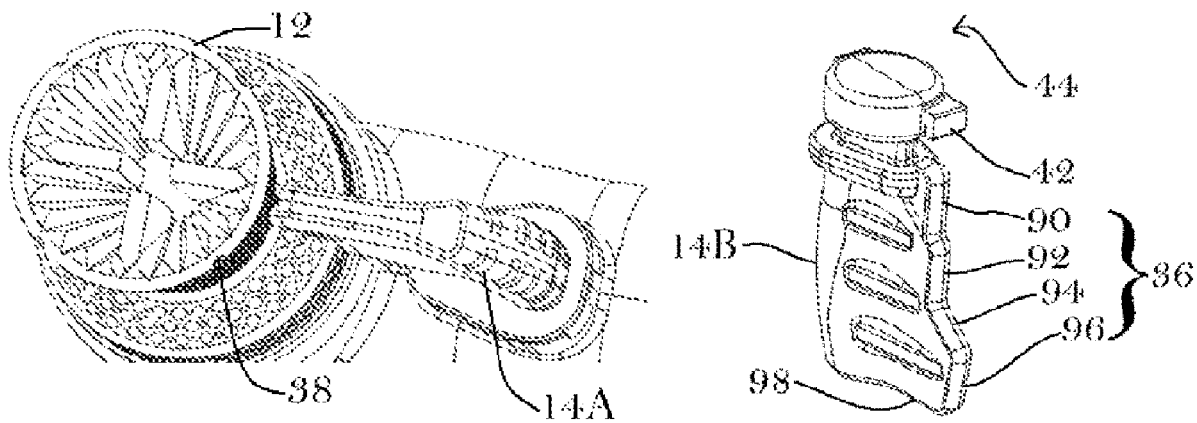

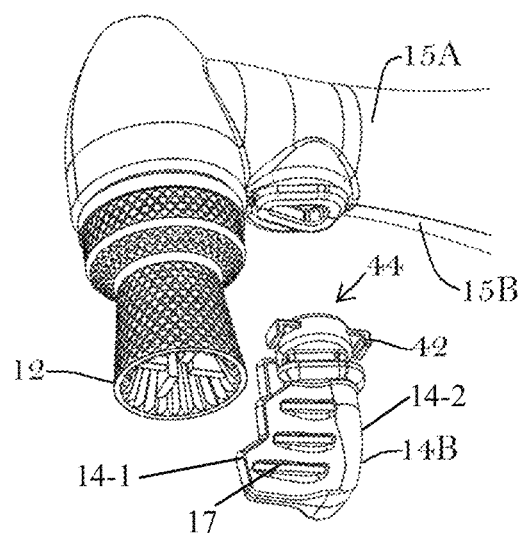
FIG. 7
(Amended)

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 7, line 4-Column 7, line 8:

*As shown in FIG. 7, the splatter guard 14B in some embodiments may comprise ribs 17 formed on a surface of the splatter guard, the ribs disposed between its proximate edge 14-1 and its distal edge 14-2.* In some embodiments, rather than being a separate piece, the splatter guard 14B may be molded integrally with one of the housing halves 15A, 15B. This design would ensure that the splatter guard 14B is properly positioned and aligned, and not moved or removed from the hand piece 10.

THE DRAWING FIGURES HAVE BEEN CHANGED AS FOLLOWS:

FIG. 7 Reference characters 14-1, 14-2 and 17 have been added.

AS A RESULT OF REEXAMINATION, IT HAS BEEN DETERMINED THAT:

Claims 1, 13 and 18 are determined to be patentable as amended.

Claims 2-5, 9-12, 14-16 and 19, dependent on an amended claim, are determined to be patentable.

New claim 21 is added and determined to be patentable.

Claims 6-8, 17 and 20 were not reexamined.

1. A hand piece comprising:
a rotating member having a longitudinal axis; and
a splatter guard attached to a housing of the hand piece, the splatter guard having a proximate edge, proximate the rotating member, and a distal edge, distal the rotating member, the proximate edge extending lengthwise along the longitudinal axis and abutting the rotating member, wherein
the distal edge has a first thickness and the proximate edge has a second, smaller thickness; [and]
the proximate edge, at an end distal to the housing, terminates prior to a longitudinal end of the rotating member; *and*
*the proximate edge following a contour of and exterior of the rotating member and abutting the rotating member from a longitudinal start of the rotating member, where the rotating member attaches to the housing of the hand piece, opposite the longitudinal end thereof, to a distal end of the splatter guard.*

13. A splatter guard, comprising:
a mounting end for attachment to a hand piece;
a distal end opposite the mounting end;
a distal edge spanning between a connection end and the distal end, the distal edge being distal to a cleaning cup when the splatter guard is attached to the hand piece, the cleaning cup having a longitudinal axis; [and]
a proximate edge spanning between the connection end and the distal end, the proximate edge extending lengthwise along the longitudinal axis and abutting the cleaning cup when the splatter guard is attached to the hand piece; *and*
*ribs formed on a surface of the splatter guard, the ribs disposed between the proximate edge and the distal edge,* wherein
the proximate edge has a first thickness and the distal edge has a second, greater thickness; and
the distal end of the proximate edge terminates prior to a longitudinal end of the cleaning cup.

18. A dental cleaning tool comprising:
a cleaning cup having a longitudinal axis; and
a splatter guard attached to a housing of the hand piece, the splatter guard having a proximate edge, proximate the cleaning cup, and a distal edge, distal the cleaning cup, the proximate edge extending lengthwise along the longitudinal axis of the cleaning cup and abutting the cleaning cup, the splatter guard including a mounting end for attachment to the dental cleaning tool and a distal end opposite the mounting end, wherein
the proximate edge, at an end distal to the housing, terminates prior to a longitudinal end of the rotating member;
*the proximate edge following a contour of and exterior of the rotating member and abutting the rotating member from a longitudinal start of the rotating member, where the rotating member attaches to the housing of the hand piece, opposite the longitudinal end thereof, to a distal end of the splatter guard;*
the distal edge has a first thickness and the proximate edge has a second, smaller thickness; and
the distal end of the proximate edge terminates prior to a longitudinal end of the cleaning cup.

*21. A hand piece comprising:*
*a rotating member having a longitudinal axis; and*
*a splatter guard attached to a housing of the hand piece, the splatter guard having a proximate edge, proximate the rotating member, and a distal edge, distal the rotating member, the proximate edge extending lengthwise along the longitudinal axis and abutting the rotating member, the splatter guard further including ribs formed on a surface of the splatter guard, the ribs disposed between the proximate edge and the distal edge, wherein*
*the distal edge has a first thickness and the proximate edge has a second, smaller thickness; and*
*the proximate edge, at an end distal to the housing, terminates prior to a longitudinal end of the rotating member.*

* * * * *